US012702667B2

(12) United States Patent
Esni et al.

(10) Patent No.: US 12,702,667 B2
(45) Date of Patent: Aug. 11, 2026

(54) FOCAL ADHESION KINASE INHIBITOR AS A THERAPEUTIC AGENT IN DIABETES

(71) Applicant: University of Pittsburgh—Of the Commonwealth System of Higher Education, Pittsburgh, PA (US)

(72) Inventors: Farzad Esni, Pittsburgh, PA (US); Jing Hu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/485,773

(22) PCT Filed: Feb. 12, 2018

(86) PCT No.: PCT/US2018/017842
§ 371 (c)(1),
(2) Date: Aug. 13, 2019

(87) PCT Pub. No.: WO2018/148666
PCT Pub. Date: Aug. 16, 2018

(65) Prior Publication Data
US 2020/0046700 A1 Feb. 13, 2020

Related U.S. Application Data

(60) Provisional application No. 62/458,470, filed on Feb. 13, 2017.

(51) Int. Cl.
*A61K 31/506* (2006.01)
*A61K 31/136* (2006.01)
*A61K 31/4015* (2006.01)
*A61K 31/4439* (2006.01)
*A61K 31/5377* (2006.01)
*A61P 5/50* (2006.01)

(52) U.S. Cl.
CPC .......... *A61K 31/506* (2013.01); *A61K 31/136* (2013.01); *A61K 31/4015* (2013.01); *A61K 31/4439* (2013.01); *A61K 31/5377* (2013.01); *A61P 5/50* (2018.01)

(58) Field of Classification Search
CPC ..... A61P 5/50; A61K 31/136; A61K 31/4015; A61K 31/4439; A61K 31/5377
See application file for complete search history.

(56) References Cited

U.S. PATENT DOCUMENTS

2006/0094682 A1* 5/2006 Westwick ................. A61P 9/10 514/44 A
2006/0247241 A1* 11/2006 Garcia-Echeverria ...................... A61P 37/08 544/122
2013/0158005 A1* 6/2013 Heinrich .................. A61P 7/00 514/210.21
2015/0071918 A1* 3/2015 McLaughlin ........ G01N 33/574 424/133.1
2016/0346282 A1 12/2016 Pachter et al.

OTHER PUBLICATIONS

Steffes et al (Diabetes Care, 2003; 26:832-836) (Year: 2003).*
Davidson (Current Medical Research and Opinion, 2004; 20(1):1919-1927) (Year: 2004).*
Cai et al (Diabetes, 2012; 61:1708-1718) (Year: 2012).*
Daoud et al (Placenta, 2008; 29:862-870) (Year: 2008).*
Cerosimo et al (Current Diabetes Reviews, 2014; 10:2-42) (Year: 2014).*
Seino et al (Proc. Jpn. Acad., Ser. B, 2010; 86:563-577) (Year: 2010).*
FDA (FDA Office of Women's Health, Diabetes Medicines, 2015) (Year: 2015).*
Schwartz (Diabetes Care, 2016; 39:179-186) (Year: 2016).*
Hameed et al (World J Diabetes, 2015; 6(4):598-612) (Year: 2015).*
Munir et al (Expert Opin Pharmacother, 2015; 16(15):2331-2341) (Year: 2015).*
Mori et al., "Hyperglycemia-induced alteration of vascular smooth muscle phenotype," *Journal of Diabetes and Its Complications*, 16: 65-68, Apr. 1, 2002.
Zhao et al., "Signal transduction by focal adhesion kinase in cancer," *Cancer Metastatis* Rev. 28: 35-49, Jan. 24, 2008.

* cited by examiner

*Primary Examiner* — Rayna Rodriguez
(74) *Attorney, Agent, or Firm* — Klarquist Sparkman, LLP

(57) ABSTRACT

It is disclosed herein that a FAK inhibitor induces conversion of acinar cells into beta cells. Methods are provided for increasing beta cell proliferation by administering an effective amount of a FAK inhibitor to a subject in need thereof. Methods are also provided for treating a subject with diabetes or at risk of developing diabetes, comprising administering to the subject a therapeutically effective amount of a FAK inhibitor.

22 Claims, 7 Drawing Sheets

| | Diabetic mice | Recovered | Not Recovered |
|---|---|---|---|
| **STZ** | 10 | 3/10 (30%) | 7/10 (70%) |
| **STZ + FAKi** | 10 | 9/10 (90%) | 1/10 (10%) |

FOCAL ADHESION KINASE INHIBITOR AS A THERAPEUTIC AGENT IN DIABETES

CROSS REFERENCE TO RELATED APPLICATIONS

This is the U.S. National Stage of International Application No. PCT/US2018/017842, filed Feb. 12, 2018, which was published in English under PCT Article 21(2), which in turn claims the benefit of U.S. Provisional Application No. 62/458,470, filed Feb. 13, 2017, which is herein incorporated by reference in its entirety.

ACKNOWLEDGMENT OF GOVERNMENT SUPPORT

This invention was made with government support under grant Nos. DK103002 and DKI01413 awarded by the National Institutes of Health. The government has certain rights in the invention.

FIELD

This relates to the field of diabetes, specifically to methods of treating a subject with or at risk of diabetes by administering a Focal Adhesion Kinase (FAK) inhibitor (FAKi) to the subject.

BACKGROUND

A mammalian pancreas is composed of two subclasses of tissue: the exocrine cells of the acinar tissue and the endocrine cells of the islets of Langerhans. The exocrine cells produce digestive enzymes that are secreted through the pancreatic duct to the intestine. The islet cells produce polypeptide hormones that are involved in carbohydrate metabolism. The islands of endocrine tissue that exist within the adult mammalian pancreas are termed the islets of Langerhans. Adult mammalian islets are composed of five major cell types, α, β, δ, PP, and ε cells. These cells are distinguished by their production of glucagon, insulin, somatostatin, pancreatic polypeptide, and ghrelin, respectively. The microenvironment of the islets of Langerhans, including proximity to blood vessels, is uniquely suited for the endocrine function of these cell types.

Diabetes mellitus results from the failure of cells to transport endogenous glucose across their membranes either because of an endogenous deficiency of insulin or an insulin receptor defect. Type 1 diabetes (T1D) is caused by the destruction of β cells, which results in insufficient levels of endogenous insulin. Current treatment of individuals with clinical manifestation of diabetes attempts to emulate the role of the pancreatic D cells in a non-diabetic individual. Generally, treatment of a diabetic individual involves monitoring blood glucose levels and using injected bovine, porcine, or cloned human insulin as required. Despite such intervention, there is often a gradual decline in the health of diabetics. Diabetes afflicts millions of people in the United States alone, and there is a clear need to provide additional treatments for this disease.

SUMMARY

Disclosed herein is the surprising finding that administration of a FAK inhibitor, such as an inhibitor of the kinase function of FAK, to a subject increases the number of functional beta-cells in the pancreas of the subject and decreases blood glucose levels in an animal model of diabetes. Accordingly, in some embodiments, a method is provided for the treatment of a subject having or at risk of developing diabetes. The methods include administering to the subject an inhibitor of FAK, for example a small molecule inhibitor of the kinase function of FAK.

In some embodiments, administering the FAK inhibitor to the subject increases a number of insulin producing beta cells in the pancreas of the subject, such as in the islets of Langerhans. In further embodiments, administering a FAK inhibitor results in the conversion of pancreatic acinar cells into insulin producing beta cells. The acinar-derived beta cells integrate into and embed themselves within the microenvironment of the islets of Langerhans.

The foregoing and other objects, features, and advantages of the invention will become more apparent from the following detailed description, which proceeds with reference to the accompanying figures.

BRIEF DESCRIPTION OF THE DRAWINGS

(FIG. 2A) The presence of tomato-red labeled insulin expressing cells shows that these cells are the progeny of acinar cells. Mouse strains are E1aCreERT2; R26-$CAG^{Tomato}$ created by crossing the E1aCreERT2 into $R26^{Tomato}$ mice. Pancreatic acinar cells are exclusively tomato-positive. Mice were treated with PF562271 FAK-inhibitor. (FIG. 2B) The indicated area highlights tomato-negative endocrine islet of Langerhans.

DETAILED DESCRIPTION

Figure 1:
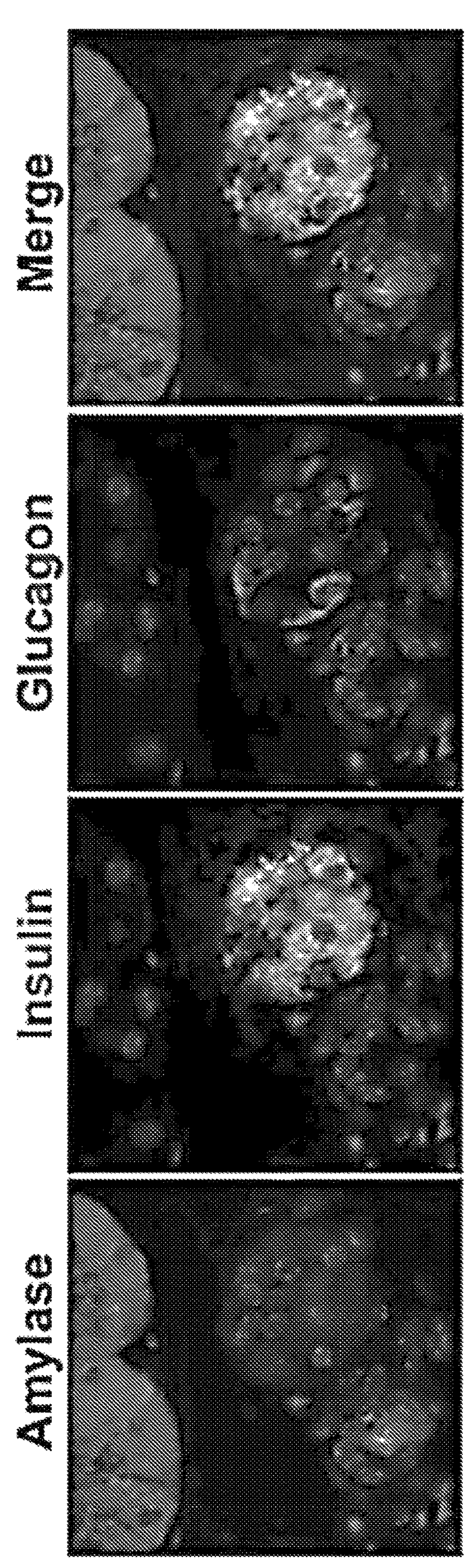
FIG. 1: Conditional knock-out of FAK in the pancreas results in cells co-expressing the acinar marker amylase with beta-cell marker insulin. Mouse strains are PdxCre; FAK-floxed.

It is disclosed herein that treatment with Focal Adhesion Kinase (FAK) inhibitor can lead to the conversion of pancreatic acinar cells into functional insulin-producing beta cells. In some embodiments, the FAK inhibitor is an inhibitor of FAK kinase activity (e.g., PF562271, available from Medkoo, Cat. No. 202228). Surprisingly, the acinar-derived beta cells embed within the islets of Langerhans microenvironment, conferring distinct advantages beyond mere insulin production. Prior studies have shown that, for example, upon transfection by a cocktail of transcription factors, acinar cells may convert into insulin-producing cells without any sign of migration. However, the acinar-derived, insulin-producing cells disclosed herein migrate and infiltrate the pre-existing islets. To be functional, beta cells need to be in proximity to blood vessels. The islets of Langerhans are one of the most vascular structures in the body. Following FAKi treatment, the acinar-derived, insulin-producing cells are found within islets, indicating that these cells are close to the vessels and, similar to the original beta cells, should sense blood glucose levels. Without being bound by theory, the methods can result in blood glucose normalization through increased beta cell numbers. Thus, subjects having or at risk of developing diabetes may be treated with a FAK inhibitor.

Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

To facilitate review of the various embodiments of this disclosure, the following explanations of specific terms are provided:

Acinar Cells: The exocrine cells of the pancreas. Acinar cells secrete enzymes important in the digestion of food. Acinar cells are positioned adjacent to a series of ducts that lead into the pancreatic duct. In normal pancreatic tissue, the location of acinar cells is distinct from the islets of Langerhans.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease, such as diabetes. Used in a generic sense, it includes treating agents, prophylactic agents, and replacement agents. A therapeutic agent can be a small molecule, for example an inhibitor of FAK. A Pharmaceutical agent is a chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care,* 22(4):623-34 at pages 626-27, herein incorporated by reference.

Beta (β) cells: Mature insulin producing endocrine cells found in the islets of Langerhans. In embodiments, insulin producing cells within the islets may be derived or converted from acinar cells. These "acinar-derived beta cells" mimic the insulin secretion and islets localization of beta cells, but it should be understood they may be otherwise distinct from native beta cells. Beta cells as used herein may refer to "acinar-derived" beta cells or native beta cells.

Diabetes mellitus (Diabetes): A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes." Type 1 diabetes mellitus is characterized by loss of the insulin-producing $ cells (also referred to herein as beta cells), leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:

a. Fasting plasma glucose level≥7.0 mmol/l (126 mg/dl);
b. Plasma glucose≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%

Endocrine: Tissue which secretes regulatory hormones directly into the bloodstream without the need for an associated duct system (e.g., islets of Langerhans).

Exocrine: Secretory tissue which distributes its products, such as enzymes, via an associated duct network. The exocrine pancreas is the part of the pancreas that secretes enzymes required for digestion. The exocrine cells of the pancreas include the acinar cells and basophilic cells, which produce secretin and cholecystokinin.

Expand: A process by which the number or amount of cells is increased due to cell division. Similarly, the terms "expansion" or "expanded" refers to this process. The terms "proliferate," "proliferation" or "proliferated" may be used interchangeably with the words "expand," "expansion," or "expanded."

Focal Adhesion Kinase (FAK): Also known as protein tyrosine kinase 2 (PTK2) and focal adhesion kinase 1 (FAK1; e.g., OMIM 600758), FAK is a protein kinase involved in cellular adhesion and migration. An exemplary FAK amino acid sequence is shown in GENBANK® accession No: AAA58469.1 (human), incorporated by reference herein as present in the database on Jan. 31, 2017. Other exemplary FAK sequences include rat and mouse amino acid sequences shown in GENBANK® accession Nos: NP_037213.1 and NP_032008.2, respectively, as well as human, rat, and mouse nucleic acid sequences shown in GENBANK® accession Nos: L13616.1, NM_013081.2, and NM_007982.2, respectively (incorporated by reference herein as present in the database on Jan. 19, 2018). Species variants, homologues, allelic forms, mutant forms, and equivalents thereof, including conservative substitutions, additions, and deletions therein not adversely affecting the structure or function are also included.

FAK inhibitor: Also referred to as FAKi herein. A FAK inhibitor may be any agent that interferes with FAK function, for example, decreasing its enzymatic functioning. FAK inhibitors may be small molecules, peptides, polynucleotides, antibodies, or fragments thereof. FAK inhibitors may function to block the kinase domain of FAK. Blockade of the FAK kinase domain results in decreased FAK kinase activity.

Insulin: A protein hormone involved in the regulation of blood sugar levels that is produced by pancreatic beta cells. In vivo, insulin is produced as a precursor proinsulin, consisting of the B and A chains of insulin linked together via a connecting C-peptide. Insulin includes only the B and A chains. Exemplary insulin sequences are provided in GENBANK® Accession NO. NM_000207.2 (human) and NM_008386.3 (mouse), and are incorporated by reference herein as present in the database on Feb. 13, 2017. Exemplary nucleic acid sequences encoding insulin are provided in GENBANK® Accession No: NM_000207.2 (human) and NM_008386.3 (mouse), and are incorporated by reference herein as present in the database on Feb. 13, 2017. Additional exemplary insulin rat amino acid and nucleotide sequences are provided in GENBANK® Accession Nos. AAA41440.1 and NM_019129.3, respectively (incorporated by reference herein as present in the database on Jan. 19, 2018). The term insulin also encompasses species variants, homologues, allelic forms, mutant forms, and equivalents thereof, including conservative substitutions, additions, and deletions therein not adversely affecting the structure or function.

Islets of Langerhans: Also known as pancreatic islets, the islets of Langerhans are small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the a cells, 0 cells, 6 cells, PP cells, and E cells. Histologically, in rodents, the islets of Langerhans consist of a central core of β cells surrounded by an outer layer of a cells, 6 cells, and PP cells. The structure of human islets of Langerhans is different and distinct from rodents. The islets of Langerhans are also sometimes referred to herein as "islets." Islets are further characterized by close proximity to blood vessels, resulting in increased efficiencies of hormone release.

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the a (glucagon producing), (insulin producing) 6 (somatostatin producing) or PP (pancreatic polypeptide producing) cells. Additional subsets produce more than one pancreatic hormone, such as, but not limited to, a cell that produces both insulin and glucagon; a cell that produces insulin, glucagon, and somatostatin; or a cell that produces insulin and somatostatin.

Pharmaceutically acceptable carriers: The pharmaceutically acceptable carriers useful in this invention are conventional. *Remington: The Science and Practice of Pharmacy*, by Loyd V. Allen, Pharmaceutical Press New York, NY, 22nd Edition (2013), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pII buffering agents and the like, for example sodium acetate or sorbitan monolaurate.

Pre-diabetes: A state in which some, but not all, of the criteria for diabetes are met. For example, a subject can have impaired fasting glycaemia or impaired fasting glucose (IFG). Subjects with fasting glucose levels from 110 to 125 mg/dl (6.1 to 6.9 mmol/l) are considered to have impaired fasting glucose. Subjects with plasma glucose at or above 140 ng/dL (7.8 nmol/L), but not over 200 mg/dL (11.1 mmol/L), two hours after a 75 g oral glucose load are considered to have impaired glucose tolerance.

Predisposition for diabetes: A subject that is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 $kg/m^2$); habitual physical inactivity; race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., The Expert Committee on the Diagnosis and Classification of Diabetes Mellitus, Diabetes Care, 26(suppl 1): s5-s20 (2003), and American Diabetes Association, Diabetes Care, 25(1): S5-S24 (2002), both of which are incorporated herein by reference.

Preventing, treating, or ameliorating a disease: "Preventing" a disease (such as type 1 diabetes) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus, or other active compound that has been isolated from a cell, cell culture medium, or other crude preparation and subjected to fractionation to remove various components of the initial preparation, such as proteins, cellular debris, and other components.

Subject: Any mammal, such as humans, non-human primates, pigs, sheep, cows, rodents, and the like that is to be the recipient of the particular treatment. An "animal" is a living, multi-cellular vertebrate organisms, a category that includes, for example, mammals and birds. The term mammal includes both human and non-human mammals. Similarly, the term "subject" includes both human and veterinary subjects. In two non-limiting examples, a subject is a human subject or a murine subject.

Therapeutically effective amount: A quantity of a specified pharmaceutical or therapeutic agent (e.g. a FAK inhibitor) sufficient to achieve a desired effect in a subject, or in a cell, being treated with the agent, such as increasing insulin production. The amount of agent, such as FAK inhibitors, that is an amount sufficient to prevent, treat (including prophylaxis), reduce and/or ameliorate the symptoms and/or underlying causes of any of a disorder or disease. In one embodiment, a "therapeutically effective amount" is sufficient to reduce or eliminate a symptom of a disease, such as diabetes. In another embodiment, an effective amount is an amount sufficient to overcome the disease itself. The therapeutically effective amount of the agent will be dependent on several factors, including, but not limited to the subject or cells being treated, and the manner of administration of the therapeutic composition. In embodiments, therapeutic efficacy may be determined by a number of mechanisms including measuring beta cell function, glucose tolerance, insulin resistance, plasma glucose levels, plasma insulin levels, serum triglycerides, free fatty acids, and/or HbA1c levels in a sample from a subject prior to, during, and/or following treatment or dosing.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

Methods of Treating Diabetes

Disclosed herein are methods of treating a subject having diabetes or at risk of developing diabetes (such as a subject with pre-diabetes or predisposition for diabetes). These methods include administering to the subject an inhibitor of FAK. In some embodiments, the inhibitor is a small molecule inhibitor of FAK kinase function. In some embodiments, the FAK inhibitor is PF562271. The subject can be a human or a veterinary subject. In some embodiments, the subject has type I diabetes. In additional, non-limiting embodiments, the FAK inhibitor is GSK2256098.

In some embodiments, the method induces pancreatic acinar cells to transform or convert into pancreatic beta cells. In additional embodiments, the acinar-derived pancreatic beta cells are embedded in islets of Langerhans. In further embodiments, treatment with a FAK inhibitor results in an increased number, or proliferation, of beta cells.

The FAK inhibitor may be administered alone or in combination with another medication or treatment (e.g., Internal Clinical Guidelines Team, Type 2 Diabetes in Adults: Management, National Institute for Health and Care Excellence: Clinical Guidelines, December 2015; National Collaborating Centre for Women's and Children's Health (UK), Diabetes (Type 1 and Type 2) in Children and Young People: Diagnosis and Management, National Institute for Health and Care Excellence: Clinical Guidelines, August 2015; and Subramanina et al., The Management of Type 1 Diabetes, NCBI Bookshelf, last updated Nov. 16, 2016, all of which are incorporated herein by reference. Additional treatments may include known therapies for the treatment of diabetes or obesity. Such therapies may include prescribed anti-diabetic lifestyle modifications. In embodiments, a FAK inhibitor may further be formulated to include inactive ingredients such as pharmaceutically acceptable, excipients, emulsifying agents, pH buffers, fillers, etc.

In further embodiments, methods of treating a subject with diabetes or a risk of developing diabetes with a FAKi further include monitoring of beta cell function, glucose tolerance, insulin resistance, plasma glucose levels, plasma insulin levels, serum triglycerides, free fatty acids, and/or HbA1c levels prior to, during, and/or following FAK inhibitor treatment.

For in vivo delivery, a FAK inhibitor can be formulated into a pharmaceutical composition and will generally be administered locally or systemically. In some embodiments, the FAK inhibitor is administered orally. In other embodiments, administration is via intravenous injection. In some embodiments, the subject has diabetes, such as type 1 diabetes.

In some embodiments, methods are provided for increasing a number of insulin-secreting cells in the pancreas, such as in the islets of Langerhans. Not to be bound by theory, administration of FAKi is thought to convert or transform pancreatic acinar cells into insulin-secreting beta cells in the islets. In some embodiments, these insulin-secreting, acinar-derived beta cells in the islets mimic native pancreatic beta cells in a subject, though they may be distinguishable from native beta cells. These methods include administering a FAK inhibitor to the subject to increase the number of insulin-secreting cells in the pancreas of the subject (such as in the islets of Langerhans).

In additional embodiments, methods are provided for treating diabetes type 1, diabetes type 2, or pre-diabetes in a subject. The subject can be any mammalian subject, including human and veterinary subjects. The subject can be a child or an adult. The method can include selecting a subject of interest, such as a subject with diabetes or at risk of developing diabetes. The subject can also be administered an additional therapy, for example a therapy used in the treatment of diabetes or obesity, such as insulin. The method can include measuring beta cell number prior to, during, and/or following treatment.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care,* 33:S11-61, 2010, incorporated herein by reference).

Appropriate doses depend on the subject being treated (e.g., human or nonhuman primate or other mammal), age and general condition of the subject to be treated, the severity of the condition being treated, and/or the mode of administration of the FAK inhibitor, among other factors. An appropriate effective amount can be readily determined by one of skill in the art. Thus, a "therapeutically effective amount" will fall in a relatively broad range that can be determined through clinical trials. The method can include measuring an outcome, such as insulin production, improvement in a fasting plasma glucose tolerance test, or pancreatic beta cell number. The method can include administering other therapeutic agents, such as insulin. The method can also include having the subject make lifestyle modifications.

In some embodiments, FAK inhibitor is administered once daily, twice daily, or more. In some embodiments, a single FAK inhibitor dose may be about 10 mg, 20 mg, 30 mg, 40 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, or more. Doses may be administered with or without food.

The dose, of course, depends on the efficiency of absorption, rate of metabolism, severity of the disease state, and clinical factors. Effective dosages can be readily established by one of ordinary skill in the art through routine trials establishing dose response curves. Prior clinical trials have utilized FAK inhibitor PF562271 in a treatment for advanced solid tumors (J. Infante et al., Safety, Pharmacokinetic, and Pharmacodynamic Phase I Dose-Escalation Trial of PF-00562271, an Inhibitor of Focal Adhesion Kinase, in Advanced Solid Tumors, J. Clin. Oncology, Vol. 30(13), May 1, 2012, included in its entirety by reference herein.)

Dosage treatment may be a single dose schedule or a multiple dose schedule to ultimately deliver the amount specified above. Moreover, the subject may be administered as many doses as appropriate. Treatment may be delivered over a course of hours, days, months, or years. One of skill in the art can readily determine an appropriate number of doses to administer.

The pharmaceutical compositions can contain a FAK inhibitor, such as PF562271, and/or inactive ingredients including a pharmaceutically acceptable excipient. Such excipients include any pharmaceutical agent that does not itself induce the production of antibodies harmful to the individual receiving the composition and that may be administered without undue toxicity. Pharmaceutically acceptable excipients include, but are not limited to, liquids, such as water, saline, glycerol, and ethanol. Pharmaceutically acceptable salts can be included therein, for example, mineral acid salts, such as hydrochlorides, hydrobromides, phosphates, sulfates, and the like, and the salts of organic acids, such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in *Remington: The Science and Practice of Pharmacy*, by Loyd V. Allen, Pharmaceutical Press New York, NY, 22nd Edition (2013).

FAK Inhibitors

A FAK inhibitor may be any agent that interferes with FAK function, such as decreasing its enzymatic function or activity. FAK inhibitors may be small molecules, peptides, polynucleotides, antibodies, or fragments or derivatives thereof. Example FAK inhibitors are described in Sulzmaier et al. (Nature Reviews: Cancer, 14:598-610 (2014), incorporated herein by reference in its entirety). FAK inhibitors may function to block the kinase domain of FAK. An exemplary FAK inhibitor that functions by blocking the kinase activity of FAK is PF562271 (also known as PF-562271, PF-271, and VS-6062; CAS #: 939791-38-5; available from Medkoo, Cat. No. 202228). The structure of PF562271 is shown below in its benzenesulfonate salt form.

PF562271

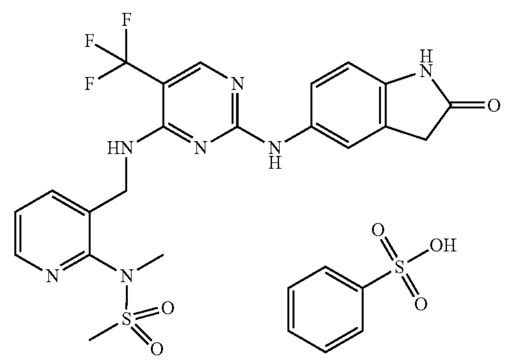

Additional example FAK inhibitors include:

GSK2256098 (also GSK-2256098; CAS #: 1224887-10-8; available from MedChem Express, Cat No. HY-100498). GSK2256098 is an inhibitor of FAK kinase activity. The structure of GSK2256098 is shown below.

GSK2256098

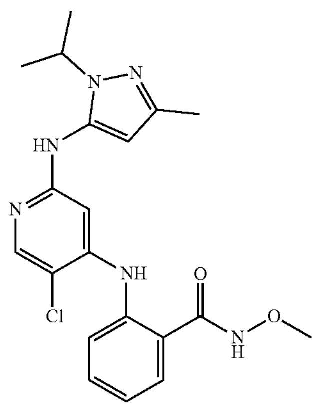

NVP-TAC544 (disclosed in International Pat. App. No. WO2004/080980). NVP-TAC544 is an inhibitor of FAK kinase activity. The structure of NVP-TAC544 is shown below.

NVP-TAC544

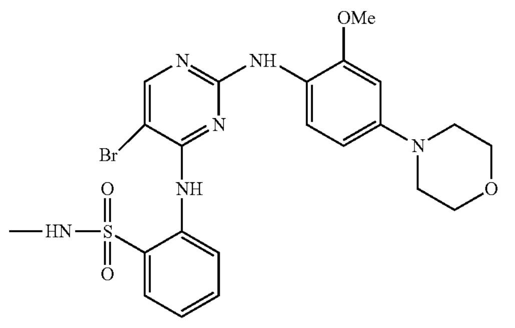

PF-573228 (CAS #: 869288-64-2; available from Selleckchem.com, Cat. No.: S2013). PF-573228 is an inhibitor of FAK kinase activity. The structure of PF-573228 is shown below.

PF-573228

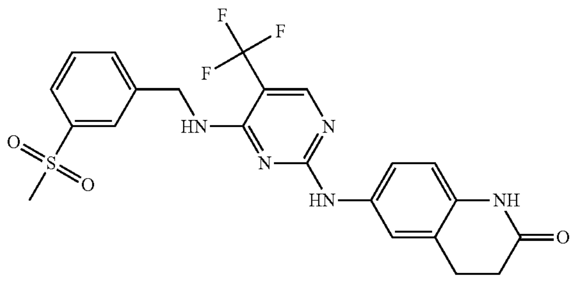

TAE226 (CAS #: 761437-28-9; available from Selleckchem.com, Cat. No.: S2820). TAE226 is an inhibitor of FAK kinase activity. The structure of TAE226 is shown below.

TAE226

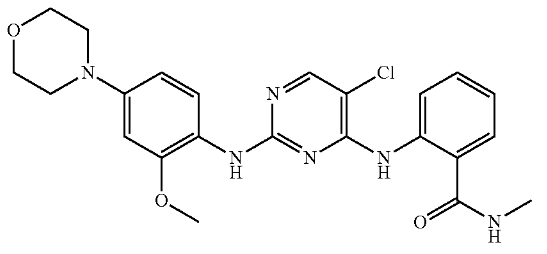

VS-4718 (CAS #: 1061353-68-1, available from selleckchem.com Cat. No.: S7653). VS-4718 is an inhibitor of FAK kinase activity. The structure of VS-4718 is shown below.

VS-4718

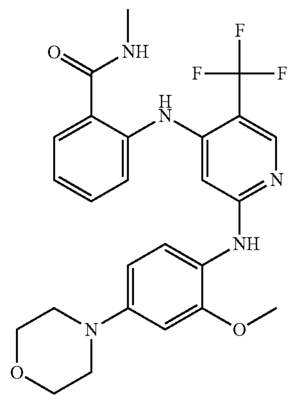

PF-04554878 (also known as VS-6063 and deactinib; CAS #: 1073154-85-4; available from selleckchem.com Cat. No.: S7654). PF-04554878 is an inhibitor of FAK kinase activity. The structure of PF-04554878 is shown below.

PF-04554878

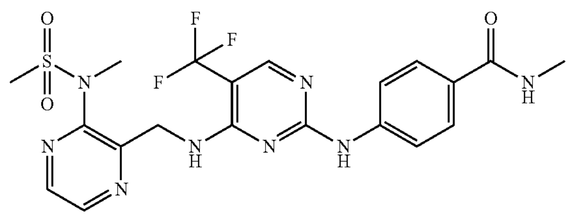

Y11 (CAS #: 1086639-59-9; available from MedKoo Cat. No.: 406462). The structure of Y11 is shown below.

Y11

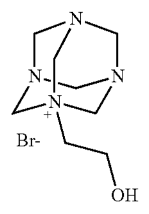

Y15 (also known as compound 14, CAS #: 4506-66-5; available from Sigma Aldrich Cat. No.: SML0837). The structure of the Y15 tetrahydrochloride salt is shown below.

Y15

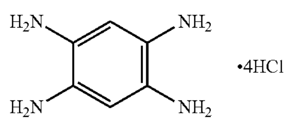

EXAMPLES

Insulin is a key regulator of glucose homeostasis and is produced by pancreatic beta cells. Insufficient insulin leads to diabetes mellitus, a metabolic disease that affects at least 200 million people worldwide (Pipeleers, D. et al. *Ann N Y Acad Sci* 958, 69-76 (2002); Zaret, K. S. & Grompe, M. *Science* 322, 1490-1494, doi:10.1126/science.1161431 (2008); Weir, G. C. & Bonner-Weir, S. *J Am Optom Assoc* 69, 727-732 (1998); Ackermann, A. M. & Gannon, M. *J Mol Endocrinol* 38, 193-206, doi:38/2/193 [pii]10.1677/JME-06-0053 (2007); Pipeleers, D. et al. *Diabetes Obes Metab* 10 Suppl 4, 54-62, doi:10.1111/j.1463-1326.2008.00941.x (2008); Pipeleers, D. & Ling, Z. *Diabetes Metab Rev* 8, 209-227 (1992)). The fundamental objective of diabetes treatment is to preserve and restore a functional beta cell mass, perhaps through beta cell replacement therapy. However, beta cell replacement may fall short in type I diabetes (TID) due to persistent autoimmunity against the new beta cells (with preexisting primed immune cells ready to attack any newly delivered beta cell) (Pipeleers, D. et al. *Ann N Acad Sci* 958, 69-76 (2002); Zaret, K. S. & Grompe, M. *Science* 322, 1490-1494, doi:10.1126/science.1161431 (2008); Weir, G. C. & Bonner-Weir, S. *J Am Optom Assoc* 69, 727-732 (1998); Ackermann, A. M. & Gannon, M. *J Mol Endocrinol* 38, 193-206, doi:38/2/193 [pii]10.1677/JME-06-0053 (2007); Pipeleers, D. et al. *Diabetes Obes Metab* 10 Suppl 4, 54-62, doi:10.1111/j.1463-1326.2008.00941.x (2008)). In fact, this form of renewed autoimmune attack has been found to be particularly aggressive (Purcell, L. J. & Mottram, P. L. *Transplant Proc* 27, 2166-2167 (1995)). Unfortunately, a clinically applicable strategy leading to an increase in beta cell mass without the need for immunosuppression has yet to be developed for T1D. Such a clinical strategy would be highly advantageous. T1D could be cured without the need for immunosuppression. In addition, such a strategy would avoid the need for allogeneic islet transplants, which can exacerbate an immune attack against future transplants of any kind, especially kidney transplant (Campbell, P. M. et al., *Am J Transplant* 7, 1242-1248, doi:10.1111/j.1600-6143.2007.01777.x (2007)).

Although great efforts have been made to identify, isolate, and purify beta cell progenitors in the adult pancreas (Kushner, J. A., Weir, G. C. & Bonner-Weir, S. *Cell Metab* 11, 2-3, doi:S1550-4131(09)00379-9 [pii]10.1016/j.cmet.2009.12.005 (2010); Kopp, J. L. et al. *Cell Cycle* 10, 1921-1927 (2011)), accumulating evidence does not support a substantial contribution of beta cell neogenesis to a functional beta cell mass in the adult pancreas (Dor, Y., Brown, J., Martinez, O. I. & Melton, D. A. *Nature* 429, 41-46, (2004); Teta, M., Rankin, M. M., Long, S. Y., Stein, G. M. & Kushner, J. A. *Dev Cell* 12, 817-826, (2007); Meier, J. J. et al. *Diabetes* 57, 1584-1594, (2008); Georgia, S. & Bhushan, A. *J Clin Invest* 114, 963-968, doi:10.1172/JCI22098 (2004); Xiao, X. et al. *J Biol Chem* 288, 25297-25308, (2013); Xiao, X. et al. *J Clin Invest* 123, 2207-2217, (2013); Xiao, X. et al. *Diabetes* 62, 1217-1226, (2013); Rankin, M. M. et al. *Diabetes* 62, 16341645, (2013); Solar, M. et al. *Dev Cell* 17, 849-860, (2009); Kopp, J. L. et al. *Development* 138, 653-665, (2011); Chintinne, M. et al. *PLoS One* 7, e43959, (2012); Kopinke, D. et al. *Development* 138, 431-441, (2011); Desai, B. M. et al. *J Clin Invest* 117, 971-977; Pan, F. C. et al. *Development* 140, 751-764, (2013); Cavelti-Weder, C. et al. *Endocrinology* 154, 4493-4502, (2013); Tonne, J. M. et al. *Diabetologia*, doi:10.1007/s00125-014-3416-4 (2014)), except for a few rare situations (Thorel, F. et al. *Nature* 464, 1149-1154, (2010); Baeyens, L. et al. *Nat Biotechnol* 32, 76-83, (2014); Chera, S. et al. *Nature* 514, 503-507, (2014)). Thus, a therapeutic approach may be required that allows for generation of new beta cells from other cell types.

As disclosed herein, acinar cells can be utilized as a source for beta cell replacement. Whether or not administration of FAK inhibitors provides for the reprogramming of acinar cells into insulin producing beta cells was examined. FAK inhibitors are described herein for their utility in converting acinar cells into beta cells. Furthermore, these acinar-derived beta cells embed within existing islets of Langerhans, conferring the advantages of the islet microenvironment, including proximity to blood vessels, which provides for increased efficiency of insulin secretion.

Human and rodent acinar cells can be induced in vitro to express insulin through cytokine treatment or viral-mediated expression of MAPK and STAT3 (Lemper, M. et al., Reprogramming of human pancreatic exocrine cells to beta-like cells, *Cell Death Differ,* 22, 1117-1130, doi:10.1038/cdd.2014.193 (2015); Bacyens, L. et al., In vitro generation of insulin-producing beta cells from adult exocrine pancreatic cells, *Diabetologia* 48, 49-57, doi:10.1007/s00125-004-1606-1 (2005)). Furthermore, continued cytokine release by surgically implanted pumps or transduction of mouse acinar cells in vivo with vectors encoding three transcription factors that are necessary for β cell development can induce conversion of acinar cells to functional β cells (Zhou, Q. et al., In vivo reprogramming of adult pancreatic exocrine cells to beta-cells, Nature, 455, 627-632, doi:nature07314 [pii] 10.1038/nature07314 (2008); Baeyens, L. et al., Transient cytokine treatment induces acinar cell reprogramming and regenerates functional beta cell mass in diabetic mice, Nat Biotechnol, 32, 76-83, doi:10.1038/nbt.2747 (2014)). However, long-term persistence of acinar-derived β-like cells requires reprogramming a significant number of acinar cells (Li, W. et al., Long-term persistence and development of induced pancreatic beta cells generated by lineage conversion of acinar cells, *Nat Biotechnol* 32, 1223-1230, doi:10.1038/nbt.3082 (2014)). Thus, the key to successful reprogramming is to create a large number of newly formed F-like cells, which enable the cells to form islet structures and their own niche environment (Li, W. et al., Long-term persistence and development of induced pancreatic beta cells generated by lineage conversion of acinar cells, *Nat Biotechnol,* 32, 1223-1230, doi:10.1038/nbt.3082 (2014)). The correlation between the number of functional β cells and longevity is not surprising, as inter-islet communication and enhanced cell-cell contact are important for f cell function (Hopcroft, D. W. et al., Structure-function relationships in pancreatic islets: support for intraislet modulation of insulin secretion, Endocrinology, 117, 2073-2080, doi:10.1210/endo-117-5-2073 (1985); Ravier, M. A. et al., Loss of connexin36 channels alters beta-cell coupling, islet synchronization of glucose-induced Ca2+ and insulin oscillations, and basal insulin release, *Diabetes* 54, 1798-1807 (2005); Meda, P. et al., Rapid and reversible secretion changes during uncoupling of rat insulin-producing cells, *J Clin Invest* 86, 759-768, doi:10.1172/JCI114772 (1990); Konstantinova, I. et al., EphA-Ephrin-A-mediated beta cell communication regulates insulin secretion from pancreatic islets, Cell, 129, 359-370 (2007)).

Example 1

Materials and Methods

Mice: Mice used in these studies were maintained according to protocols approved by the University of Pittsburgh Institutional Animal Care and Use Committee.

Rosa26$^{CAGTomato}$ (B6.Cg-Gt(Rosa)26Sortm9(CAG-tdTomato)Hze) (Madisen et al., 2010), FAK$^{fl/fl}$ (Cai et al., 2012), and wild type C57bl/6 mice were purchased from The Jackson Laboratory (Bar Harbor, ME). PdxCre (Criscimanna et al., 2011; Hingorani et al., 2003) mice were obtained from the Mouse Models of Human Cancer Consortium. The E1aCreERT2 strain (Criscimanna et al., 2014; Criscimanna et al., 2011) was generated as previously described (Ji, B. et al., Robust acinar cell transgene expression of CreErT via BAC recombineering, Genesis, 46, 390-395et al (2008)). The FAK-floxed strain (B6; 129X1-Ptk2tm1Lfr/Mmucd) was obtained from the Mutant Mouse Regional Resource Centers (MMRRC).

Immunofluorescence Analysis: Tissue processing, immunostaining, and quantification analysis were performed as previously described (Criscimanna et al., 2011; incorporated by reference in its entirety herein). Imaging was performed using either ZEISS Axiolmager.Z1 or ZEISS LSM 710 microscopes.

Tamoxifen treatment: E1aCreERT;R26-CAG$^{Tomato}$ mice were injected intraperitoneally with 2 mg tamoxifen on two consecutive days.

FAKi treatment: FAKi (PF562271; 50 mg/kg) was given orally to mice twice a day for 3 weeks.

Example 2

Conditional Knock-Out of Fak in the Pancreas Results in Beta Cell Markers in Pancreatic Acinar Cells In a PdxCre;FAK-floxed mouse with a conditional knock-out of FAK in the pancreas, cells co-expressed the acinar marker amylase with the beta-cell marker insulin (FIG. 1).

Example 3

Figure 2A:
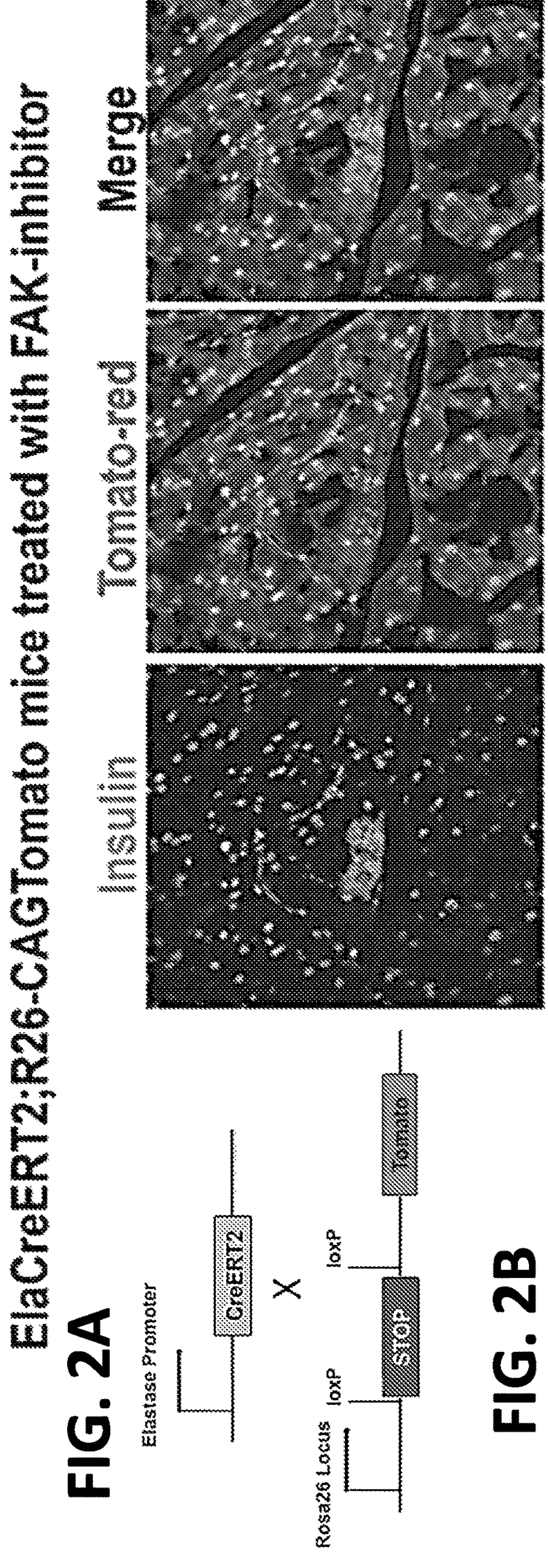
FIGS. 2A-2B: Cre-recombinase activity is specifically targeted to the pancreatic acinar cells, and their potential progenies.
Figure 2B:
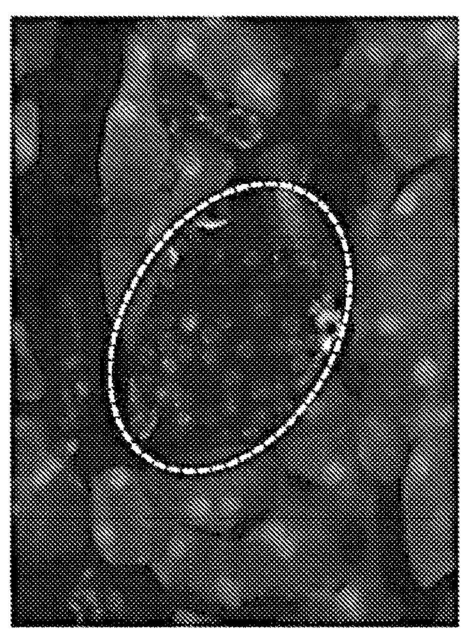

Treatment with FAK Inhibitor Results in Conversion of Pancreatic Acinar Cells to Beta Cells Cre-recombinase activity was specifically targeted to the pancreatic acinar cells and their potential progenies. The presence of tomato-red labeled insulin expression cells shows that these cells are progeny of acinar cells (FIG. 2A). The mouse strains are E1aCreERT2;R26-CAG$^{Tomato}$, created by crossing the E1aCreERT2 into R26$^{Tomato}$ mice. Pancreatic acinar cells are exclusively tomato-positive. Mice were treated with PF562271 FAKi. The indicated area in FIG. 2B highlights tomato-negative endocrine islet of Langerhans.

Figure 3:
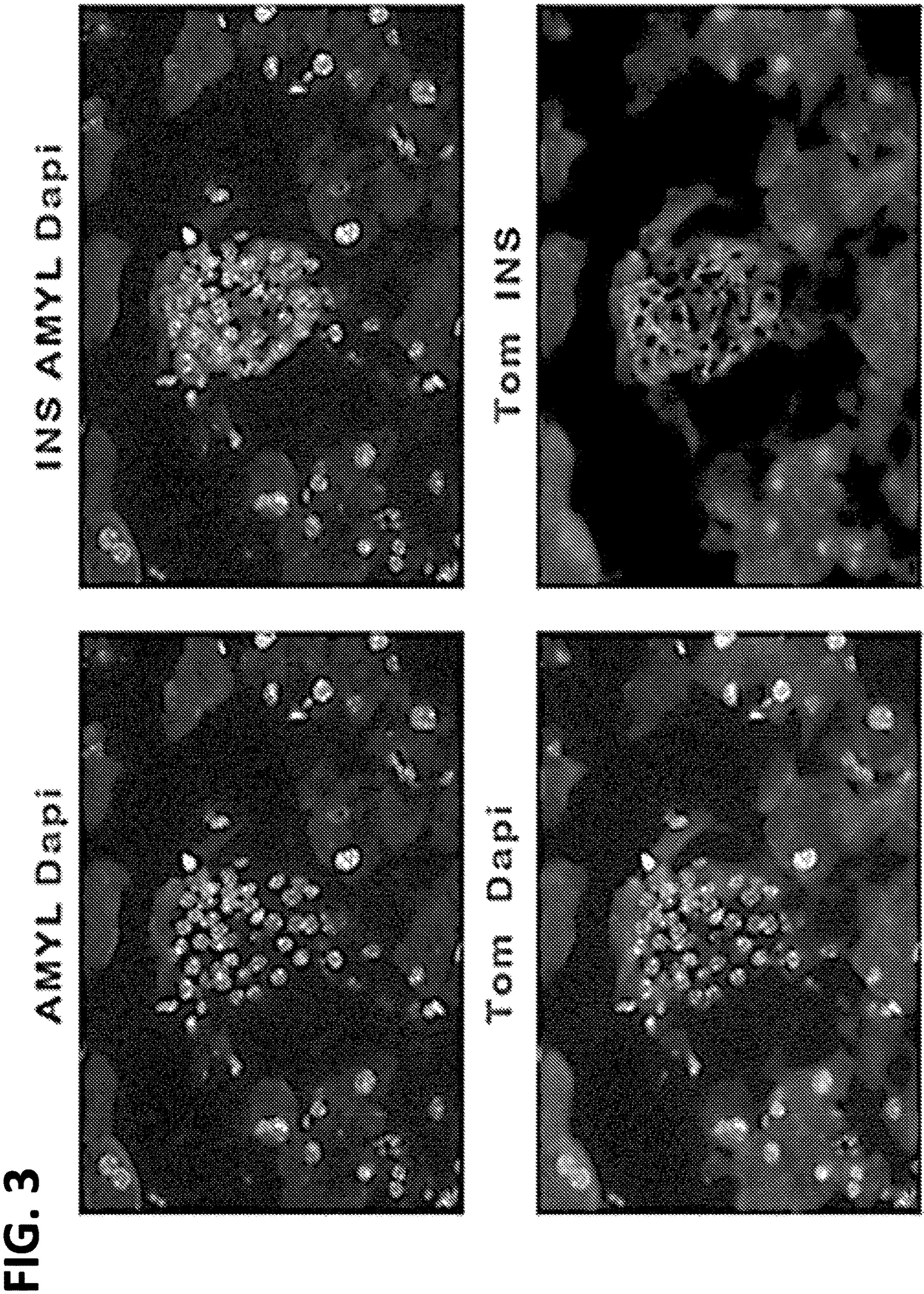
FIG. 3: Treatment of E1aCreERT2; $R26^{Tomato}$ mice with PF562271 FAK-inhibitor for three weeks induces conversion of acinar cells into insulin-producing cells. The presence of tomato-red labeled insulin-expressing cells following PF562271 FAKi treatment shows that these cells are progeny of acinar cells. The acinar-derived, insulin-positive cells no longer express amylase and are surprisingly embedded within preexisting islets.

Treatment of E1aCreERT2; R26$^{Tomato}$ mice with PF562271 FAK-inhibitor for three weeks induces conversion of acinar cells into insulin-producing cells. The presence of tomato-red-labeled insulin-expressing cells following FAKi-treatment shows that these cells are progenies of acinar cells (FIG. 3). The acinar-derived insulin-positive cells no longer expressed amylase and were surprisingly embedded within preexisting islets.

Figure 4:
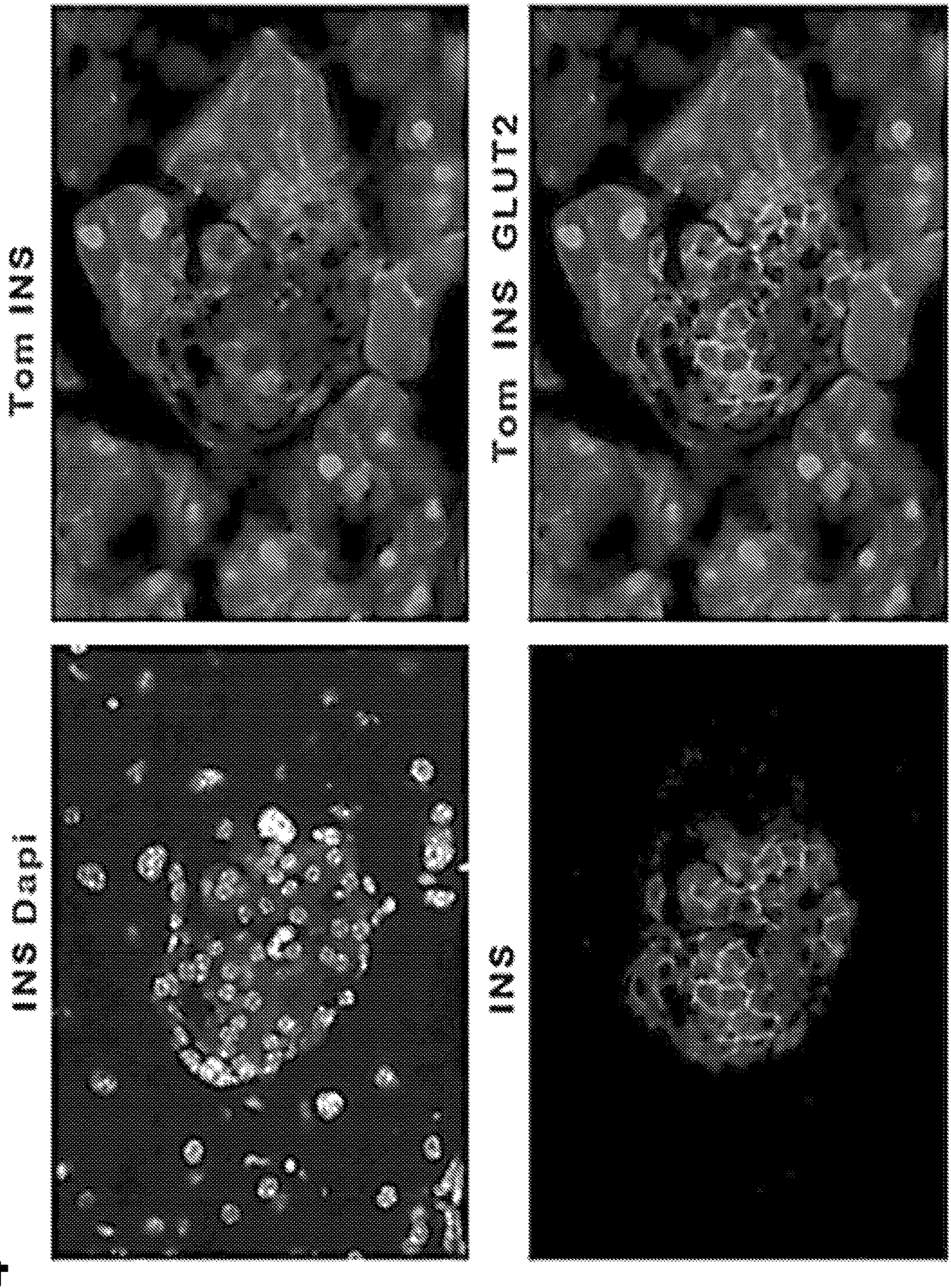
FIG. 4: The acinar-derived insulin-positive cells also express Glut2, suggesting that these cells share features with mature insulin-producing cells.

Furthermore, the acinar-derived insulin-positive cells also expressed Glut2, suggesting that these cells share features with mature insulin-producing cells (FIG. 4).

Example 4

Figure 5:
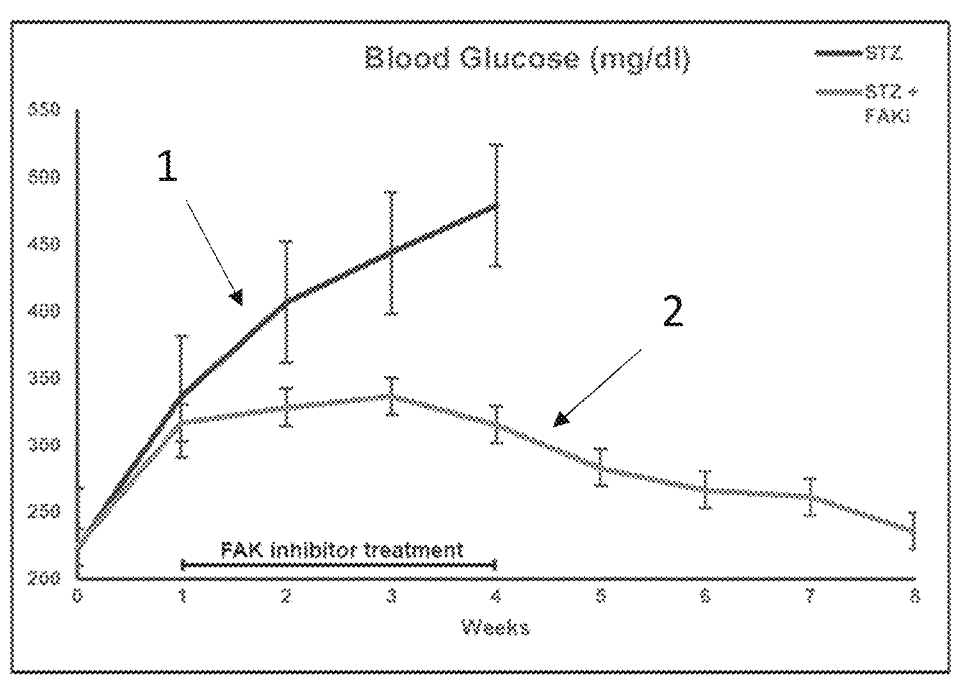
FIG. 5: E1aCreERT2; $R26^{Tomato}$ mice were treated with streptozotocin (STZ) (2-Deoxy-2-(3-methyl-3-nitrosoureido)-D-glucopyranose), a widely used compound that kills β-cells and, thus, induces diabetes in mice. As expected, the STZ-treated mice did not normalize their blood glucose levels. However, one week after FAKi treatment (mice were treated for 3 weeks), a decrease in blood glucose to normal levels was observed in the experimental cohort. The arrow indicates the initiation of FAKi treatment.

In an Induced Diabetes Mouse Model, FAK Inhibitor Treatment Results in Normalization of Blood Glucose E1aCreERT2; R26$^{Tomato}$ mice were treated with streptozotocin (STZ), a widely used compound that kills β-cells and, thus, induces diabetes in mice. As expected, the STZ-treated mice did not normalize their blood glucose levels. While mice treated with high-dose STZ do not restore normoglycemia, spontaneous recovery may occasionally occur following low-dose STZ treatment. Thus, in the DMSO-treated cohort, recovery was detected in 3/10 mice. While mice treated with high dose STZ do not restore normoglycemia, spontaneous recovery may occasionally occur following a low-dose STZ treatment. In the DMSO-treated cohort, recovery was detected in 3/10 mice. One week into FAKi-treatment, the blood glucose levels began to stabilize and gradually decreased to normal levels for 9/10 mice in the experimental cohort (FIG. 5).

The mice were treated for two additional weeks following blood glucose normalization. The bar embedded in the graph of FIG. 5 indicates the duration of FAKi treatment. Importantly, the blood glucose remained at normal levels up to a month after FAKi treatment ceased, indicating that maintaining blood glucose does not rely on continuous FAKi treatment. FAKi (50 mg/kg) was given orally to mice twice a day for 3 weeks.

Figure 6:
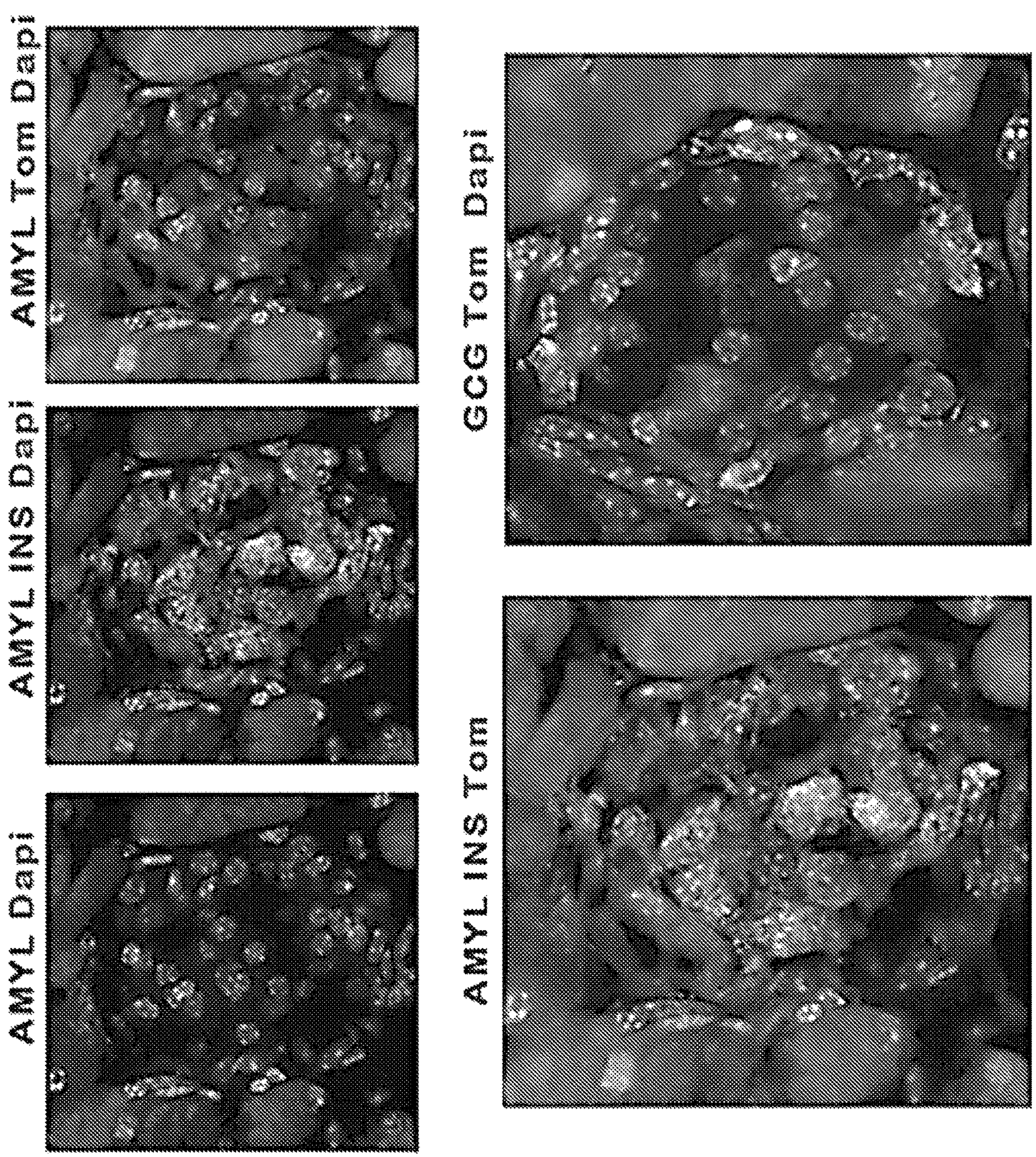
FIG. 6: Acinar-derived, insulin-producing cells could be detected among pre-existing beta-cells that had survived the STZ treatment. These images were taken 7 weeks after STZ treatment and 3 weeks after PF562271 FAKi treatment.

Importantly, acinar-derived, insulin-producing cells could be detected among pre-existing beta cells that survived the STZ treatment (FIG. 6). These data indicate that treatment with FAKi not only increases total beta cell numbers but also confers upon the acinar-derived beta cells the advantages of an islet microenvironment.

Example 5

Figures 7A, 7B, 7C:
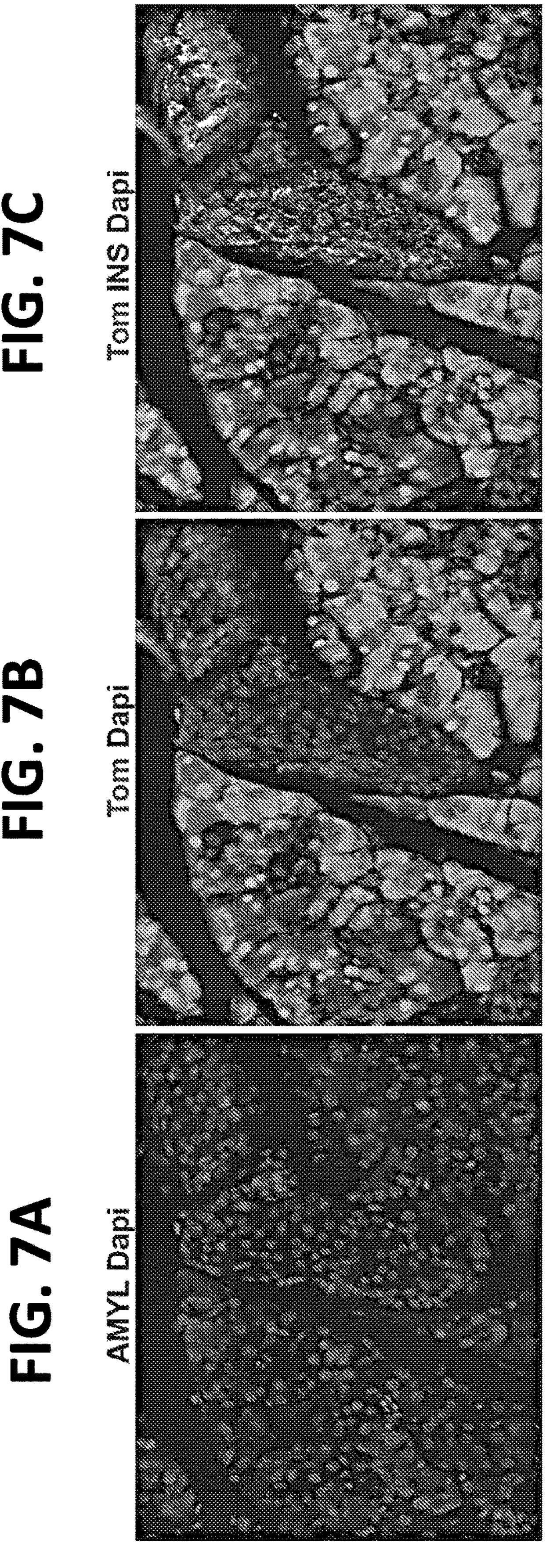
FIGS. 7A-7C: Immunostaining of sections obtained from E1aCreERT2;$R26^{Tomato}$;$FAK^{fl/wt}$ for detection of amylase (FIG. 7A), Tomato-red (FIG. 7B) or insulin (FIG. 7C). The tomato+ cells are preset within the endocrine islets.

Conditional Inactivation of the Gene Encoding FAK Leads to Acinar-Derived P-Cell Generation The FAK inhibitor used herein is a drug, and, as such, there is a risk of off-target effects. Thus, whether or not the appearance of tomato-labeled, insulin-producing cells within the islets in FAKi-treated E1aCreERT2;R26$^{Tomato}$ mice was due to ectopic activation of the elastase promoter (used to drive Cre-expression) in pre-existing β-cells, rather than conversion of acinar cells into newly formed f-cells, was examined. To evaluate the FAKi-treatment data, one allele of the FAK gene in acinar cells was conditionally knocked out by generating E1aCreERT2;R26$^{Tomato}$; FAK$^{flox/wt}$ mice. To induce Cre-recombinase activity, the CreERT-transgenic mice were IP-injected with 10 mg tamoxifen (2 mg (200 μl)×5 days). As shown in FIGS. 7A-7C, similar to FAKi-treatment, tomato+/insulin+ cells were detected as early as three weeks post-tomaxifen treatment in 3-month-old E1aCreERT2;R26$^{Tomato}$;FAK$^{flox/wt}$ mice. Thus, the tomato-labeled insulin-producing cells observed in FAKi-treated E1aCreERT2; R26$^{Tomato}$ mice are the result of pancreatic acinar-to-β-like cell conversion.

In view of the many possible embodiments to which the principles of the disclosure may be applied, it should be recognized that the illustrated embodiments are only preferred examples and should not be taken as limiting the scope. Rather, the scope of the disclosure is defined by the following claims. We therefore claim all that comes within the scope and spirit of these claims.

We claim:

1. A method for treating a subject with type 2 diabetes, comprising:

administering to the subject a therapeutically effective amount of a focal adhesion kinase (FAK) inhibitor, wherein the FAK inhibitor is PF-562271, thereby treating the type 2 diabetes in the subject.

2. The method of claim 1, further comprising selecting the subject with type 2 diabetes for treatment with the FAK inhibitor.

3. The method of claim 2, wherein the therapeutically effective amount of the FAK inhibitor converts acinar cells into beta cells in the subject.

4. The method of claim 2, wherein treating the type 2 diabetes does not require administration of the FAK inhibitor after blood glucose is normalized.

5. The method of claim 1, wherein the FAK inhibitor is administered in a dose of 75 mg, 100 mg, or 125 mg, given once or twice daily.

6. The method of claim 1, further comprising measuring beta cell function of the subject.

7. The method of claim 1, further comprising measuring glucose tolerance, insulin resistance, plasma glucose levels, plasma insulin levels, serum triglycerides, free fatty acids, and/or HbA1c levels in a sample from the subject.

8. The method of claim 1, wherein the therapeutically effective amount of the FAK inhibitor increases a number of beta cells in the subject.

9. The method of claim 1, wherein the therapeutically effective amount of the FAK inhibitor converts acinar cells into beta cells in the subject.

10. The method of claim 1, wherein the therapeutically effective amount of the FAK inhibitor increases a number of insulin-secreting cells in the islets of Langerhans of the subject.

11. The method of claim 1, wherein the subject is human.

12. The method of claim 1, wherein the therapeutically effective amount of the FAK inhibitor reduces plasma glucose levels in the subject.

13. The method of claim 1, wherein the therapeutically effective amount of the FAK inhibitor increases plasma insulin levels in the subject.

14. The method of claim 1, further comprising measuring plasma glucose levels in a sample from the subject.

15. The method of claim 1, wherein treating the type 2 diabetes does not require administration of the FAK inhibitor after blood glucose is normalized.

16. The method of claim 1, further comprising detecting acinar-derived beta cells in the subject.

17. The method of claim 1, wherein a single dose of the FAK inhibitor is administered to the subject.

18. The method of claim 1, wherein the FAK inhibitor is not administered in combination with another diabetes medication or treatment.

19. A method for treating a subject with type 2 diabetes, comprising:
- selecting the subject with type 2 diabetes for treatment,
- administering to the subject a therapeutically effective amount of PF-562271, and
- subsequently detecting acinar-derived beta cells in the subject, thereby treating the type 2 diabetes in the subject.

20. The method of claim 19, wherein the FAK inhibitor is not administered in combination with another diabetes medication or treatment.

21. The method of claim 19, wherein blood glucose level of the subject remains normalized one month after treatment with PF-562271 ceases.

22. A method for treating a subject with type 2 diabetes, comprising:
- selecting the subject with type 2 diabetes for treatment, and
- increasing an amount of acinar-derived beta cells in the subject by administering a therapeutically effective amount of PF-562271 to the subject, thereby treating the type 2 diabetes in the subject.

* * * * *